United States Patent
Hill

[19]

[11] Patent Number: 5,814,085
[45] Date of Patent: Sep. 29, 1998

[54] RATE STABILIZATION PACEMAKER

[75] Inventor: Michael R. S. Hill, Minneapolis, Minn.

[73] Assignee: Medtronic, Inc., Minneapolis, Minn.

[21] Appl. No.: 843,485

[22] Filed: Apr. 16, 1997

Related U.S. Application Data

[60] Provisional application No. 60/033,511 Dec. 19, 1996.
[51] Int. Cl.$^6$ ................................................ A61N 1/365
[52] U.S. Cl. ................................................ 607/14; 607/9
[58] Field of Search .............................. 607/7, 14, 25, 607/28

[56] References Cited

U.S. PATENT DOCUMENTS

| 4,941,471 | 7/1990 | Mehra . |
| 5,480,413 | 1/1996 | Greenhut et al. . |
| 5,545,185 | 8/1996 | Denker . |

OTHER PUBLICATIONS

"Rate Stabilization by Right Ventricular Pacing in Patients with Atrial Fibrillation", Wittkampf et al, PACE, vol.9, Nov.–Dec. 1986, Part II, pp.1147–1153.

Primary Examiner—William E. Kamm
Assistant Examiner—George R. Evanisko
Attorney, Agent, or Firm—Reed A. Duthler; Harold R. Patton

[57] ABSTRACT

A cardiac pacemaker with a rate stabilization pacing mode. The pacemaker varies the increment following a cycle ending in a sensed depolarization as a function of the underlying heart rate and may additionally vary the increment as a function of the prematurity of the most recently sensed depolarization relative to the preceding depolarization. A greater increment is generally provided if the underlying cycle length is greater, while the increment may be lessened following relatively more premature depolarizations. Prematurity may be determined by comparing the cycle (CLnew) ending in the most recently sensed depolarization with the previous cycle length (CLold), for example by calculating CLnew/CLold or CLold–CLnew. The mechanism for determining the duration of the increment provides for a more rapid return to a lower underlying heart rate, while still avoiding the short-long interval pattern sometimes associated with the onset of tachycardia.

18 Claims, 9 Drawing Sheets

RATE STABILIZATION PACEMAKER

CROSS REFERENCE TO RELATED APPLICATIONS

This application claims priority from U.S. Provisional Application No. 60/033,511 filed Dec. 19, 1996.

BACKGROUND OF THE INVENTION

This invention relates generally to cardiac stimulators and more particularly to cardiac pacemakers.

As set forth in the article "Rate Stabilization by Right Ventricular Pacing in Patients With Atrial Fibrillation", by Wittkampf et. al., published in PACE, Vol. 9, November–December, 1986, Part II, pp 1147–1153, rapid, variable ventricular rhythms have negative hemodynamic consequences. The Wittkampf article therefore proposes VVI pacing with a self adapting pacing rate selected to result in 91% of all depolarizations being paced. The article states that this methodology provides stable ventricular rates in the presence of atrial fibrillation with only a moderate increase in over-all rate. A dual chamber pacemaker which addresses the same problem is disclosed in U.S. Pat. No. 5,480,413, issued to Greenhut et al. This device detects the presence of atrial tachyarrhythmia and a concurrent irregular ventricular depolarization and raises the ventricular pacing rate until the ventricular rhythm is regularized. Both of these prior art approaches operate by analyzing a series of preceding ventricular depolarizations and gradually modulating the pacing rate until a stable ventricular rhythm is accomplished.

U.S. Pat. No. 4,941,471 issued to Mehra et al and U.S. Pat. No. 5,545,185 issued to Denker disclose pacemakers designed to prevent the short-long depolarization interval patterns accompanying PVC's, which are often associated with the onset of ventricular tachyarrhythmias. These pacemakers, unlike those in the Wittkampf and Greenhut references, modulate the pacing interval on a beat by beat basis to provide pacing interval slightly longer than a preceding intrinsic interval. In the Mehra patent, the pacing modality is disclosed as continuously activated. In the Denker patent, the pacing modality is activated only on detection of a long-short interval pattern.

SUMMARY OF THE INVENTION

The present invention is directed to an improvement to the rate stabilization pacemakers described in the above-cited Mehra and Denker patents. In these patents, when rate stabilization pacing is active, the pacemaker defined escape interval differs from a preceding intrinsic escape interval or pacer defined escape interval (hereafter both referred to as "cycles") by a preset increment dT, which may either be a fixed value or a percentage of the duration of the preceding cycle or cycles. While these pacemakers accomplish the desired result of preventing the short-long cycle patterns sometimes associated with the onset of tachycardias, they do not take into account the underlying heart rate or the degree of prematurity of the sensed heart depolarization in calculating the value of the increment. The present invention varies the increment following a cycle ending in a sensed depolarization as a function of the underlying heart rate and may additionally vary the increment as a function of the prematurity of the most recently sensed depolarization relative to the preceding depolarization. A greater increment is generally provided if the underlying cycle length is greater, while the increment may be lessened following relatively more premature depolarizations. Prematurity may be determined by comparing the cycle (CLnew) ending in the most recently sensed depolarization with the previous cycle length (CLold), for example by calculating CLnew/CLold or CLold−CLnew. The mechanism of the present invention for determining the duration of the increment provides for a more rapid return to a lower underlying heart rate, while still avoiding the short-long interval pattern sometimes associated with the onset of tachycardia. It is believed that this mechanism of controlling the escape intervals in a rate stabilization pacing mode may assist in avoiding arrhythmias by reducing the amount of pacemaker-induced fluctuation of the heart's refractory period.

In a first embodiment of the invention, the value of dT may be set directly as a function (f1) of the average cycle length of cycles preceding the cycle (CLnew) ending in the sensed depolarization. For example dT may be set equal to A*(avgCL)−D, where A may be a programmed or fixed value and D may be a programmed or fixed value or may be a programmed or fixed fraction of the minimum pacemaker escape interval (Tmin).

In a second embodiment, the value of dT may be additionally modified as a function (f2) of the duration of the cycle ending in the most recently sensed depolarization and the relative prematurity of the sensed depolarization. For example, dT may be set equal to f1(avgCL)+B*(CLnew/CLold))−D, or dT may be set equal to f1(avgCL)+B/(CLold−CLnew)−D, where B may be a programmed or fixed value and D may be a programmed or fixed value or may be a programmed or fixed fraction of the minimum pacemaker escape interval (Tmin). Alternatively, dT may be set equal to f1(avgCL)−B*(CLold/CLnew)−D or f1(avgCL)−B/(CLold−CLnew)−D. In some embodiments, the present value of CLnew may additionally influence the determination of dT, which for example could be set equal to f1(avgCL)+B*(CLnew*(CLnew/CLold))−D. The values of the various constants and/or variables are chosen to accomplish variation of the increment dT primarily as a function of the underlying rate, with the increment reduced with increasing relative prematurity. Other calculation mechanisms to accomplish similar variation of dT may also be employed.

The invention may be practiced using either sensed and paced atrial depolarizations or ventricular depolarizations to define the cycle lengths used to calculate the increment dT and the pacemaker's escape interval. The invention may also be usefully practiced in devices which regulate the maximum pacing escape interval (Tmax) and the minimum pacing escape interval (Tmin) as a function of a sensor of cardiac demand such as an activity sensor, a blood temperature sensor, an oxygen saturation sensor, a minute volume sensor or a stroke volume sensor.

DETAILED DESCRIPTION OF THE DRAWINGS

Figure 1:
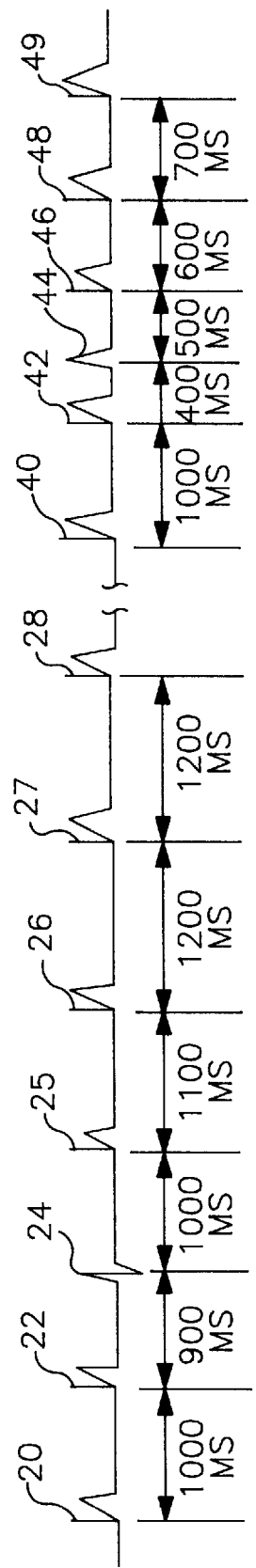
FIG. 1 shows a simulated EKG strip illustrating the operation of the pacemaker described in the Mehra patent cited above.

FIG. 1 illustrates the operation of a pacemaker according to the prior Mehra patent, cited above. To understand the operation of a pacemaker according to the Mehra patent and the present invention, some basic timing intervals must be understood. As used herein, Tmax indicates the maximum allowable interval between a sensed beat and a paced beat or between two paced beats. Te is the escape interval that the pacemaker calculates with the beginning of each new cardiac cycle, and determines the delivery of the next pacing pulse. dT is an incremental interval used in calculation of the interval Te. For purposes of FIG. 1, the interval corresponding to the minimum pacing rate (Tmax) is set at 1200 ms and the value for incrementing the pacing interval (dT) with each cycle is set at 100 ms. At the beginning of the trace at pacing pulse 20, the effective escape interval (Te) is set at 1000 ms. After the expiration of this period at 22, a pacing pulse is generated and Te is incremented by 100 ms, to 1100 ms. A naturally conducted depolarization occurs at 24,900 ms after the paced depolarization at 22. At this point, Te is recalculated, and set at 1000 ms (the previous natural escape interval plus 100 ms). The escape interval Te is similarly incremented by 100 ms at 25 and 26. At 26, Te=Tmax. In the absence of underlying heart activity, Te will remain at Tmax, as illustrated at 27 and 28. This illustrates the basic functioning of the pacing mode of a pacemaker according to the Mehra patent. With the beginning of each new escape interval on the occurrence of either a paced or a sensed atrial or ventricular depolarization, the subsequent pacing interval is calculated to be equal to the previous pacing interval, plus a fixed increment dT (for example 100 ms). Incrementing continues until the escape interval Te equals the minimum pacing rate interval Tmax.

The second portion of FIG. 1 illustrates the response of a pacemaker according to the Mehra patent to the occurrence of a PVC. The minimum pacing rate interval Tmax is again set at 1200 ms, and the escape interval of the pacemaker Te is set at 1000 ms at paced beat 40. After the expiration of the 1000 ms escape interval at 42, the escape interval Te is recalculated to be 1100 ms. 400 ms after the paced beat at 42, a PVC occurs at 44. At this point, the escape interval Te is recalculated to be 500 ms (the actual previous escape interval plus 100 ms). Following this 500 ms escape interval, a pacing pulse is generated at 46 and the escape interval Te is recalculated to be 600 ms. 600 ms later at 48, another paced event occurs, and the escape interval Te is similarly recalculated. As an alternative to a fixed increment dT, the Mehra patent also suggests that the increment could be a predefined proportion of the most recent cycle length, e.g. 20%.

Figure 2A:
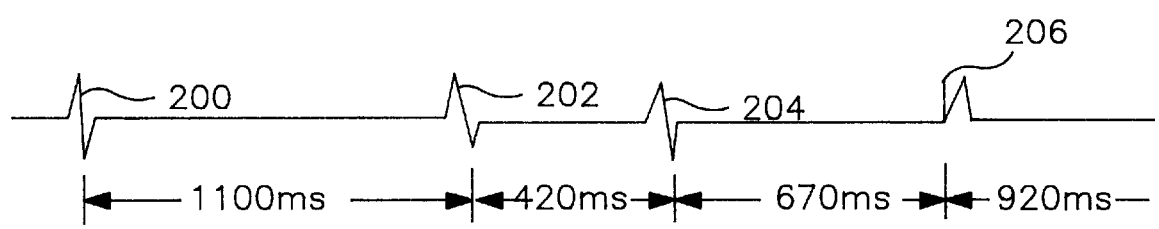
FIGS. 2a–2b are simulated EKG strips illustrating the operation of a first embodiment of pacemaker according to the present invention.
Figure 2B:

FIG. 2a and FIG. 2b are simulated electrocardiograms illustrating a first embodiment of the invention, in which the duration of the increment dT varies directly as a function of the underlying heart rate. In this case, the increment is set according to the equation dT equals 0.3(avgCL) minus 80, with avgCL calculated over the three cycles ending before the cycle in which the most recent depolarization was sensed. For purposes of FIG. 2a, it should be assumed that average duration of the three cycles preceding sensed depolarization 200 are 1,100 milliseconds, so that at depolarization 202, the value of avgCL is also 1100 ms. Following sensed depolarization 204, the microprocessor calculates a new value for dT using the preceding equation, yielding a value of 250 milliseconds for dT, such that the next escape interval is set equal to 670 milliseconds, at the expiration of which a pacing pulse is generated at 206. At 206, the microprocessor increments the escape interval again by 250 milliseconds to 920 milliseconds, and so forth.

FIG. 2b illustrates the effect of an higher underlying heart rate, on calculation of the duration of dT. It should be assumed that prior to sensed depolarization 208, the three preceding cycles had lengths of 600 milliseconds so that upon the occurrence of sensed depolarization 210, the value of avgCL is also 600 milliseconds. At 212, a relatively premature sensed depolarization occurs, 420 milliseconds following depolarization 210. Using the equation set forth, the microprocessor calculates the value of dT to be equal to 100 milliseconds, so that the escape interval is set equal to 520 milliseconds. On expiration of escape interval 214, a pacing pulse is delivered and the escape interval is again incremented by 100 milliseconds to a value of 620 milliseconds, on the expiration of which a pacing pulse is generated at 216, and so forth, illustrating the relatively smaller increment dT provided in the presence of a higher heart rate.

FIGS. 3a–3e are simulated electrograms which illustrate a first alternative embodiment of the invention, in which the value of dT is set using the equation dT equals 0.125(avgCL) +0.134(CLnew*(CLnew/CLold))−11. Using this mechanism of determining the value of the increment dT, the device provides an increment that generally increases with decreasing heart rate, but decreases as a function of the relative prematurity of the most recently sensed depolarization. FIGS. 3a–3e together illustrate the behavior of such a device, under a variety of circumstances.

Figure 3A:
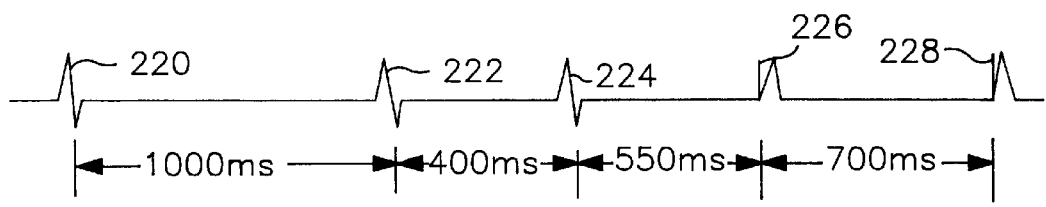
FIGS. 3a–3e are simulated EKG strips illustrating the operation of a second embodiment of a pacemaker according to the present invention.

In FIG. 3a, it should be assumed that prior to depolarization 220, the preceding 3 heart cycle lengths averaged 1,000 milliseconds, so that at depolarization 222, the value of avgCL is also 1,000 milliseconds. A relatively premature beat 224 occurs at 400 milliseconds, and the microprocessor updates the value of dT using the preceding equation, reaching a value of 150 milliseconds for the value of the increment and 550 milliseconds for the value of the escape interval. At 226 the escape interval expires and is again incremented by 150 milliseconds, to produce an escape interval of 700 milliseconds, at the expiration of which, a pacing pulse is delivered at 228.

Figure 3B:
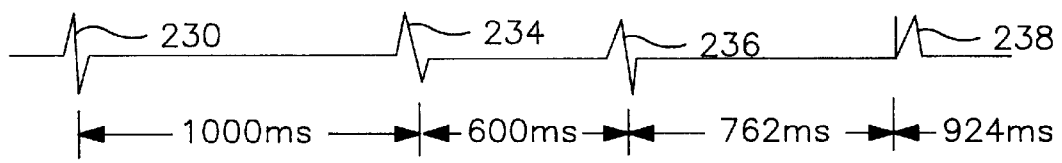

FIG. 3b illustrates a similar situation, with a relatively less premature beat. Prior to sensed depolarization 230, it should be assumed that the preceding three cycles averaged 1,000 milliseconds so that at 234, the value of avgCL is also 1,000 milliseconds. A somewhat less premature beat 236 occurs 600 milliseconds later, and using the above equation, the microprocessor calculates the value of dT to be equal to 162 milliseconds, yielding an escape interval of 762 milliseconds. Because sensed depolarization 236 was relatively less premature than sensed depolarization 224, a relatively longer increment dT is provided. On expiration of the 762 millisecond escape interval, a pacing pulse is delivered at 238, and the value of escape interval is again incremented 162 milliseconds to 924 milliseconds.

Figure 3C:
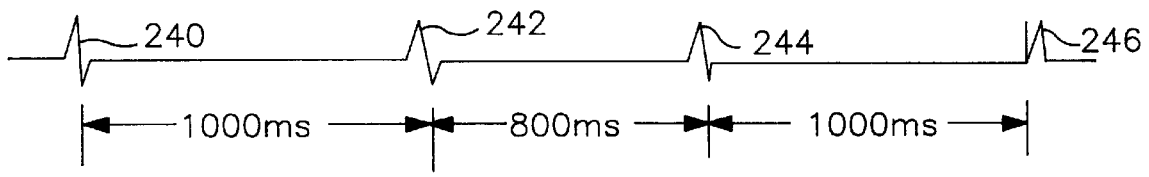

FIG. 3c illustrates the effect of a beat of relatively little prematurity, under circumstances otherwise corresponding to FIGS. 3a and 3b above. Prior to sensed depolarization 240, it should be assumed that the three preceding cycles had an average length of 1,000 milliseconds, so that at sensed depolarization 242, the value of avgCL is also 1,000 milliseconds. Sensed depolarization 244 occurs 800 milliseconds later, and the microprocessor, using the previously stated equation calculates a value for dT of 200 milliseconds, yielding an escape interval of 1,000 milliseconds, on the expiration of which a pacing pulse is generated at 246. At 246, the escape interval is recalculated again to be the lesser of the maximum escape interval Tmax or 1,200 milliseconds.

Figure 3D:
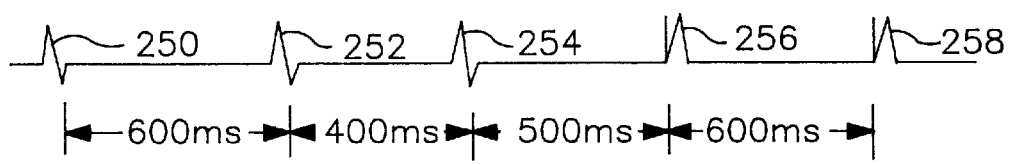

FIG. 3d illustrates the situation in which the underlying rate is substantially higher than in FIGS. 3a–c. Prior to sensed depolarization 250, it should be assumed that the preceding three cycles had an average value of 600 milliseconds so that at sensed depolarization 252, the value of avgCL is also 600 milliseconds. 400 milliseconds thereafter, a sensed beat 254 occurs, causing the microprocessor to update the value of dT using the previously stated equation, yielding a value of 100 milliseconds for dT. Because the underlying rate is substantially higher, the corresponding value of dT is substantially lower than in FIG. 3a, discussed above. The 100 millisecond increment dT is added to the escape interval to yield 500 millisecond escape interval, on the expiration of which a pacing pulse is delivered at 256. The microprocessor adds an additional 100 millisecond increment to the escape interval to define an escape interval of 600 milliseconds, on the expiration of which a pacing pulse is generated at 258, and so forth.

Figure 3E:

FIG. 3e illustrates a situation having an underlying rate intermediate that illustrated in FIGS. 1a and 1d. Prior to sensed depolarization 260, it should be assumed that the three preceding cycles had an average value of 800 milliseconds so that at 262, the value of avgCL is also 800 milliseconds. A relatively premature beat 264 occurs 400 milliseconds later, causing the microprocessor to update the value of dT to 152 milliseconds, yielding an escape interval of 552 milliseconds. It should be noted that the increments provided in a situation illustrated in FIG. 3e is intermediate the corresponding increments calculated in the circumstances illustrated in FIGS. 3a and 3d. At the expiration the 552 millisecond escape interval at 266, a pacing pulse is generated and the microprocessor updates the escape interval by adding an additional 152 milliseconds to yield an escape interval of 704 milliseconds. At the expiration of this escape interval, a pacing pulse is delivered at 268, and so forth.

FIGS. 4a–4e illustrate the operation of a third embodiment of a pacemaker according to the present invention, in the same situations illustrated in FIGS. 3a–3e. However, in this case, the value of dT is calculated using the equation dT equals 0.25 (avgCL) minus 0.125*(CLold minus CLnew) minus 25. Although the method of calculation differs substantially from that illustrated in conjunction with FIGS. 3a–3e, the overall behavior of the device is similar.

Figure 4A:
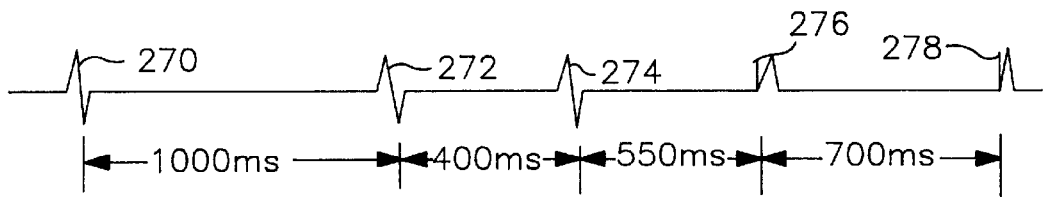
FIGS. 4a–4e are simulated EKG strips illustrating the operation of a third embodiment of a pacemaker according to the present invention.

In FIG. 4a, it should be assumed that prior to sensed depolarization 270, the preceding three cycles had an average cycle length of 1,000 milliseconds so that at sensed depolarization 272, the value of avgCL is also 1,000 milliseconds. A relatively premature beat 274 occurs 400 milliseconds later, causing the microprocessor to calculate the value of dT, using the preceding equation, yielding a value of 150 milliseconds for dT which results in a 550 millisecond escape interval. On expiration of the 550 millisecond escape interval at 276, a pacing pulse is delivered and the microprocessor updates the escape interval by adding an additional 150 milliseconds to yield a 700 millisecond escape interval. On expiration of the 700 millisecond escape interval, a pacing pulse is generated at 278, and so forth.

Figure 4B:
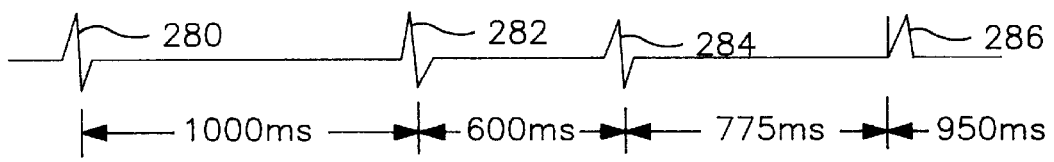

In FIG. 4b, it should be assumed that prior to sensed depolarization 280, the preceding three cycles lengths had an average duration of 1,000 milliseconds so that at sensed depolarization 282, the value of avgCL is also 1,000 milliseconds. 600 milliseconds later at 284, a sensed depolarization occurs, causing the microprocessor to update the value of dT using the preceding equation, which results in a value of 175 milliseconds for dT and an escape interval of 775 milliseconds. On expiration of the 775 millisecond escape interval, a pacing pulse is generated at 286 and the escape interval is again incremented by 175 milliseconds, and so forth.

Figure 4C:
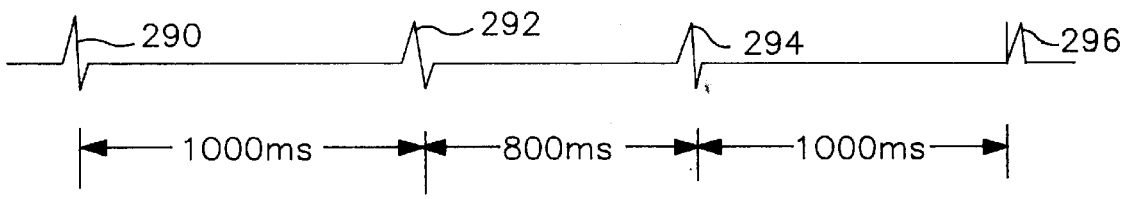

In FIG. 4c, prior to sensed depolarization 290, it should be assumed that the average cycle length of the three preceding cycles was 1,000 milliseconds, so that at sensed depolarization occurring at 292, the value of avgCL is also 1,000 milliseconds. 800 milliseconds thereafter at 294, sensed depolarization occurs of relatively little prematurity, and the microprocessor employs the preceding equation to calculate a value of 200 milliseconds for dT at a value of 1,000 milliseconds for the escape interval. At 296, on expiration of the 1,000 millisecond escape interval, the microprocessor resets the escape interval to be equal to the lesser of Tmax and 1,200 milliseconds, as noted above. FIGS. 4a, 4b and 4c, taken together, illustrate a relatively linear progression of the value of dT in the presence of the same underlying heart rate, as a function of increased prematurity, as measured by the difference between CL new and CL old.

Figure 4D:
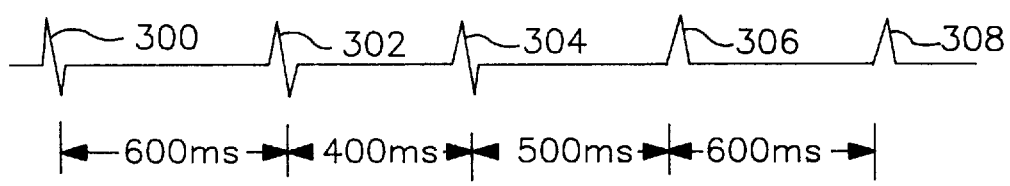

FIG. 4d illustrates the situation in which the underlying rate is substantially higher than in FIGS. 4a–c. Prior to sensed depolarization 300, it should be assumed that the preceding three cycles had an average value of 600 milliseconds so that at sensed depolarization 302, the value of avgCL is also 600 milliseconds. 400 milliseconds thereafter, a sensed beat 304 occurs, causing the microprocessor to update the value of dT using the previously stated equation, yielding a value of 100 milliseconds for dT. Because the underlying rate is substantially higher, the corresponding value of dT is substantially lower than in FIG. 4a, discussed above. The 100 millisecond increment dT is added to the escape interval to yield 500 millisecond escape interval, on the expiration of which a pacing pulse is delivered at 306. The microprocessor adds an additional 100 millisecond increment to the escape interval to define an escape interval of 600 milliseconds, on the expiration of which a pacing pulse is generated at 308, and so forth.

Figure 4E:

FIG. 4e illustrates a situation having an underlying rate intermediate that illustrated in FIGS. 4a and 4d. Prior to sensed depolarization 310, it should be assumed that the three preceding cycles had an average value of 800 milliseconds so that at 312, the value of avgCL is also 800 milliseconds. A relatively premature beat 314 occurs 400 milliseconds later, causing the microprocessor to update the value of dT to 125 milliseconds, yielding an escape interval of 525 milliseconds. It should be noted that the increments provided in a situation illustrated in FIG. 4e is intermediate the corresponding increments calculated in the circumstances illustrated in FIGS. 4a and 4d. At the expiration the 525 millisecond escape interval at 316, a pacing pulse is generated and the microprocessor updates the escape interval by adding an additional 125 milliseconds to yield an escape interval of 650 milliseconds. At the expiration of this escape interval, a pacing pulse is delivered at 318, and so forth.

The simulated electrograms of FIGS. 2a, 2b, 3a–3e and 4a–4e all illustrate implementations of the invention in which the value of dT is calculated according to the stated equations only in response to sensed beats, and stays constant after paced beats. However, alternative implementations of the invention may update the value of dT following paced beats as well, using the same equations. For example, in FIG. 2b, the value of dT could be updated after pacing pulse 214, using the preceding cycle lengths of 600 ms., 600 ms., 600 ms. and 420 ms. to calculate avgCL, using the 420 ms. interval between sensed depolarizations 210 and 212 as CLold and the 520 ms. cycle length between sensed depolarization 212 and pacing pulse 216 as CLnew. Using this methodology, the value of dT following pacing pulse 214 would be 86.5 ms., yielding an escape interval of 606.5 ms. The value of dT would then correspondingly be updated after pacing pulse 216, and so forth. Similarly, the value of dT could be updated after each paced beat in the implementations illustrated in FIGS. 3a–3e and 4a–4e.

Figure 5:
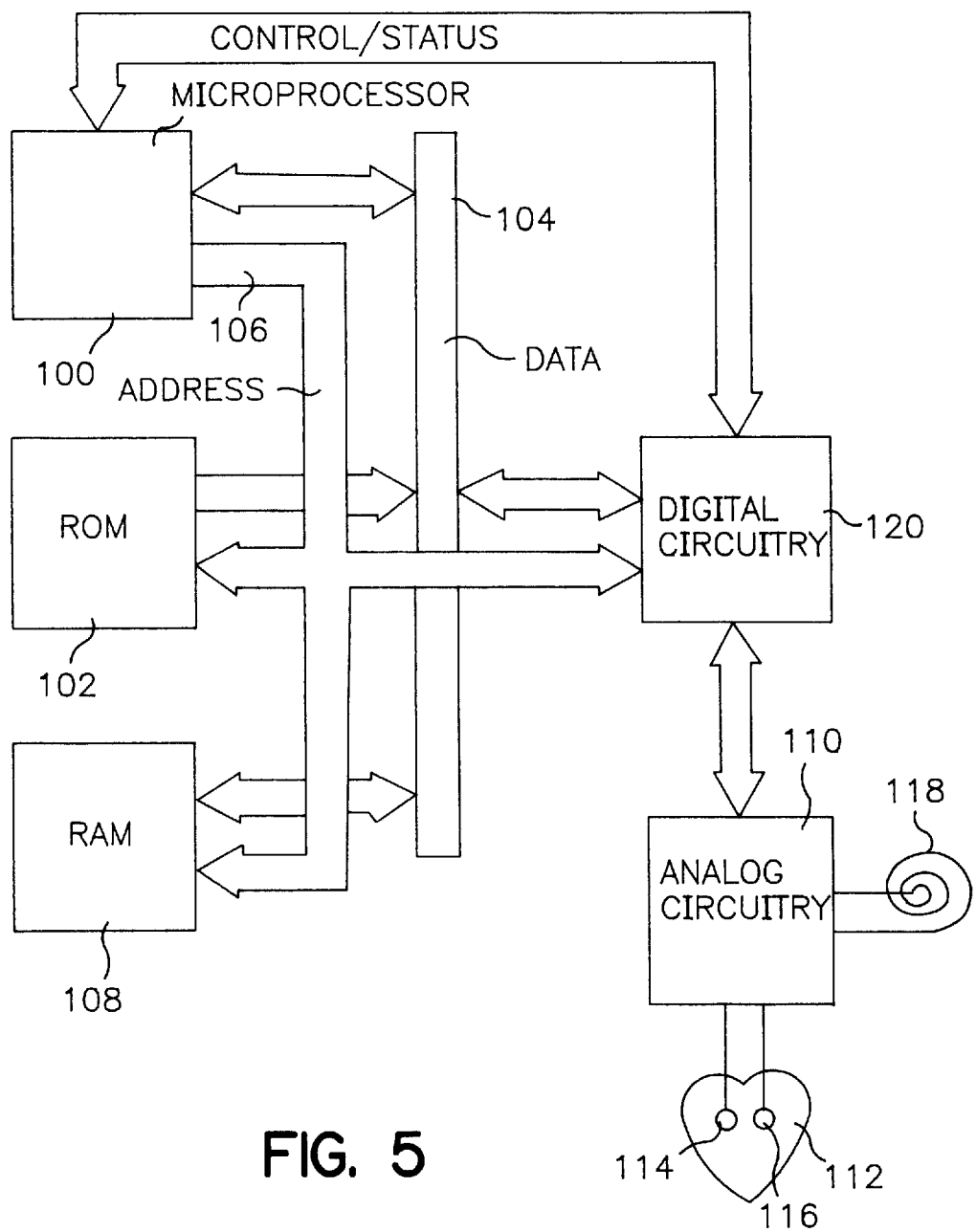
FIG. 5 is a functional block diagram of a pacemaker according to the present invention.

FIG. 5 is a block diagram of the present invention embodied in the form of a microprocessor based pacemaker. The basic architecture set forth herein is similar to that set forth in the Mehra patent, cited above. However, it is believed that one of skill in the art would be able to incorporate the present invention in microprocessor based pacemakers having differing architecture, or in pacemakers employing other analog and digital circuitry architecture. The invention is believed to reside in the method of operation, rather than in any particular physical embodiment. The basic operation of the pacemaker is controlled by the microprocessor chip 100, under control of a stored program located in the read only memory 102. The stored program is accessed by the microprocessor via the data bus 104. Access to the read only memory 102 is controlled via the address bus 106. Programmable or alterable parameters (such as Tmax) are stored in the random access memory 108. Entry of data into the random access memory 108 and read out from the random access memory 108 is controlled by microprocessor 100. The analog circuitry 110 of the pacemaker includes an output stage which generates pacing pulses to stimulate the heart and includes a sense amplifier which detects underlying heart activity. Both the output amplifier and the sense amplifier are coupled to the heart 112 by means of electrodes 114 and 116, at least one of which is mounted to or within the heart 112. Analog circuitry 110 also includes circuitry for receiving telemetry signals from and transmitting signals to an external programmer via antenna 118. Analog circuitry 110 is under the control of digital circuitry 120. Digital circuitry 120 is controlled via control/status line 122, by microprocessor 100. Digital circuitry 120 includes one or more interval counters to facilitate timing functions and triggers the operation of the output stage in analog circuitry 110 in response to time up of the pacemaker's escape interval. Digital circuitry 120 also controls the telemetry of digital data out of the pacemaker via analog circuitry 110 and controls entry of data received by analog circuitry 110 into the microprocessor 100 and random access memory 108.

Figure 6:
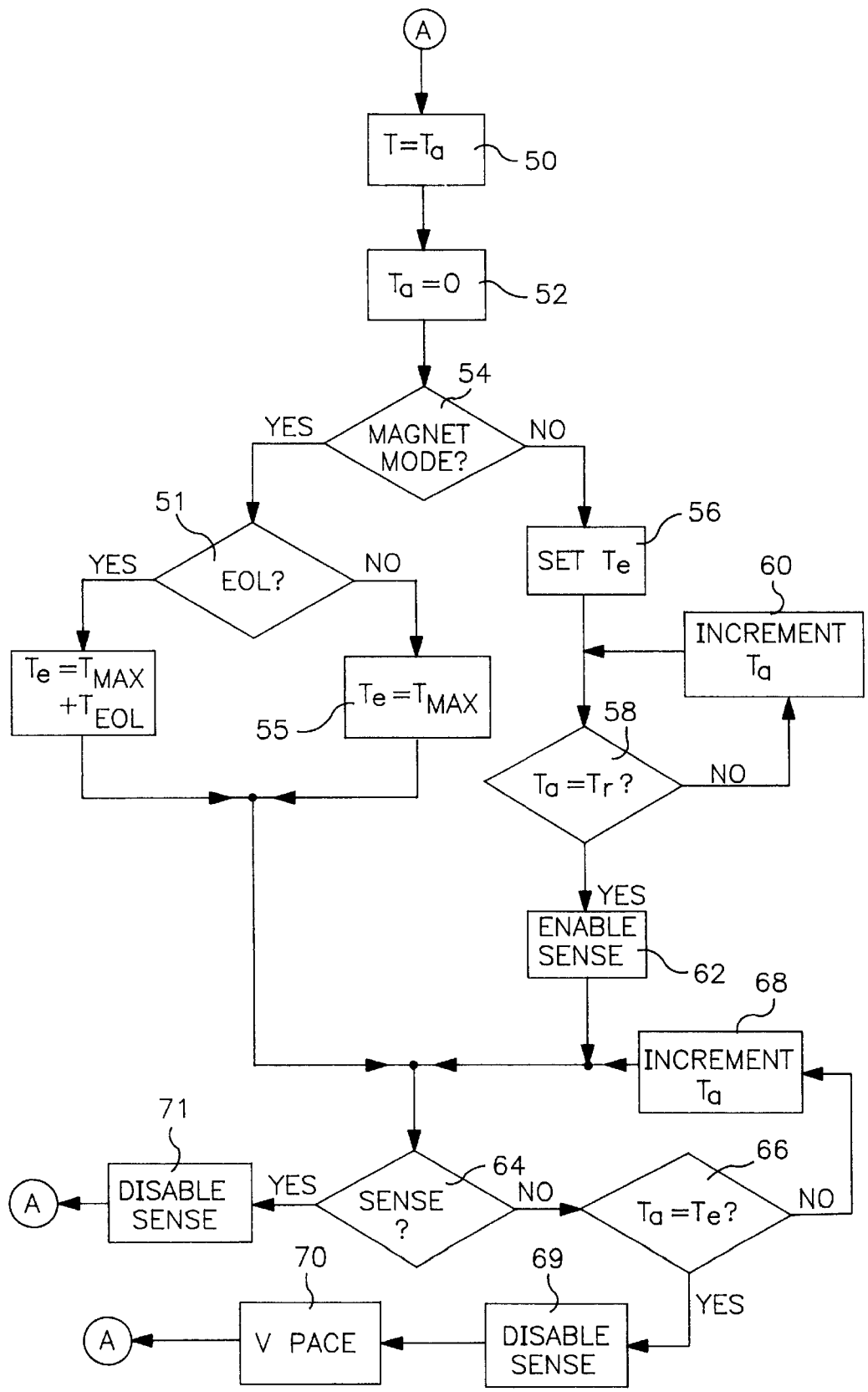
FIG. 6 is a first functional flow chart illustrating the basic operation of a pacemaker according to the present invention.

FIG. 6 illustrates a generalized flow chart of the functional operation of the pacemaker according to the present invention, as implemented in an atrial or ventricular demand pacemaker. Although the present invention may be configured in any of the currently available electronic technologies, including discrete components, custom logic circuitry, or microprocessor based circuitry, the preferred mode is believed to take the form of a microprocessor based pacemaker.

The pacemaker is provided with a basic, minimum pacing rate interval Tmax. Tmax is preferably a programmable parameter, which defines the maximum interval which may separate a paced depolarization from the immediately preceding sensed or paced depolarization. In the microprocessor based embodiment illustrated in FIG. 5, an interval counter located in the digital circuitry 120 is used to determine timing intervals, as in the above-cited Mehra patent. Tmax is therefore a count which corresponds to the desired interval of time. Typically, Tmax will correspond to intervals of 600 to 1500 ms, and typically will be about 800 to 1000 ms. Similarly, Tmin is a count corresponding to the maximum allowable pacing rate (minimum pacing interval). dT is a calculated value corresponding to the increment of time added to each successive pacing cycle, typically falling between 50 and 300 ms. "T" is the value of the timing interval counter stored at the point that a cycle ends, either with a paced beat or a sensed depolarization. "Ta" is the value held in the interval counter at any particular point in time. At the expiration of a depolarization interval, this value will be reset to 0 so that counting of the next subsequent interval may begin. "Te" is the variable corresponding to the pacemaker's operative escape interval. When Ta equals Te, a pacing pulse will be delivered. Teol is an interval of time, typically 100 ms or so which is added to the effective escape interval when the pacemaker detects the onset of end-of-life or battery depletion. Tr is the number corresponding to the refractory period, typically 100 to 500 ms. When Ta equals Tr, the pacemaker's sense amplifier is enabled so that it may detect the occurrence of the natural depolarizations.

The basic operation of the pacemaker is cyclic. The arbitrary starting point A is the time immediately following the delivery of a pacing pulse or the occurrence of a sensed depolarization. T is set equal to Ta (the actual escape interval) at 50. The interval counter is then reset at 52, with Ta reset to 0. At 54, a test is done to determine whether the pacemaker is in magnet mode.

As is typical in prior art pacemakers, it is envisioned that a pacemaker according to the present invention will display end-of-life indicating behavior in response to the presence of a magnet placed over the pacemaker. Alternatively, the presence of the programming head of a cardiac pacemaker programmer over the pacemaker could be used to trigger entry into the end-of-life indicator pacing mode. The particular choice of end-of-life behavior is not critical to practicing the invention. However, in those cases in which a change in pacing rate is chosen to indicate end-of-life, it is suggested that modification of the escape interval according to the present invention should be suspended during end-of-life checking to facilitate EKG interpretation.

Assuming that a magnet or programming head is present, the pacemaker checks to determine whether battery voltage indicates that the pacer is nearing its end-of-life at 51. If battery voltage is less than a predetermined amount, the pacemaker sets the escape interval Te equal to the maximum pacing interval Tmax plus an incremental interval Teol. If battery voltage is within normal limits, the pacemaker sets the escape interval Te equal to Tmax. Because the sense amplifier is not enabled at any time when the pacemaker is magnet mode, the pacemaker will pace asynchronously with the escape interval of either Tmax or Tmax+Teol, providing a convenient check to determine whether battery depletion is imminent.

Assuming that no magnet or programming head is present, the pacemaker determines the next escape interval Te at 56. The algorithm for so determining the escape interval is set forth in FIG. 7, below. After determining the escape interval Te, the pacemaker checks continually to determine whether the count Ta in the interval counter is equal to the refractory period count Tr, at 58. The interval counter continues to be incremented at 60, until Ta equals Tr, after which time the sense amplifier 62 is enabled at 62, so that the pacemaker may sense underlying heart activity. After enabling of the sense amplifier, the pacemaker continually checks to determine whether a depolarization has been sensed at 64 and whether the escape interval has expired at 66. Until one of these events occurs, the interval counter continues to be incremented at 68. Assuming that a depolarization is sensed prior to the expiration of the escape interval Te, the sense amplifier is disabled at 71, and the count Ta in the interval counter is stored at 50, as discussed above. The cardiac cycle is restarted thereafter at 52, by resetting the interval counter. If, on the other hand, the escape interval expires prior to the sensing of a depolarization, the sense amplifier is disabled at 69 and a pacing pulse is generated at 70. The time at which the pacing pulse is generated is stored at 50, as discussed above, and the timing cycle is restarted at 52 by resetting the interval counter to 0.

Figure 7:
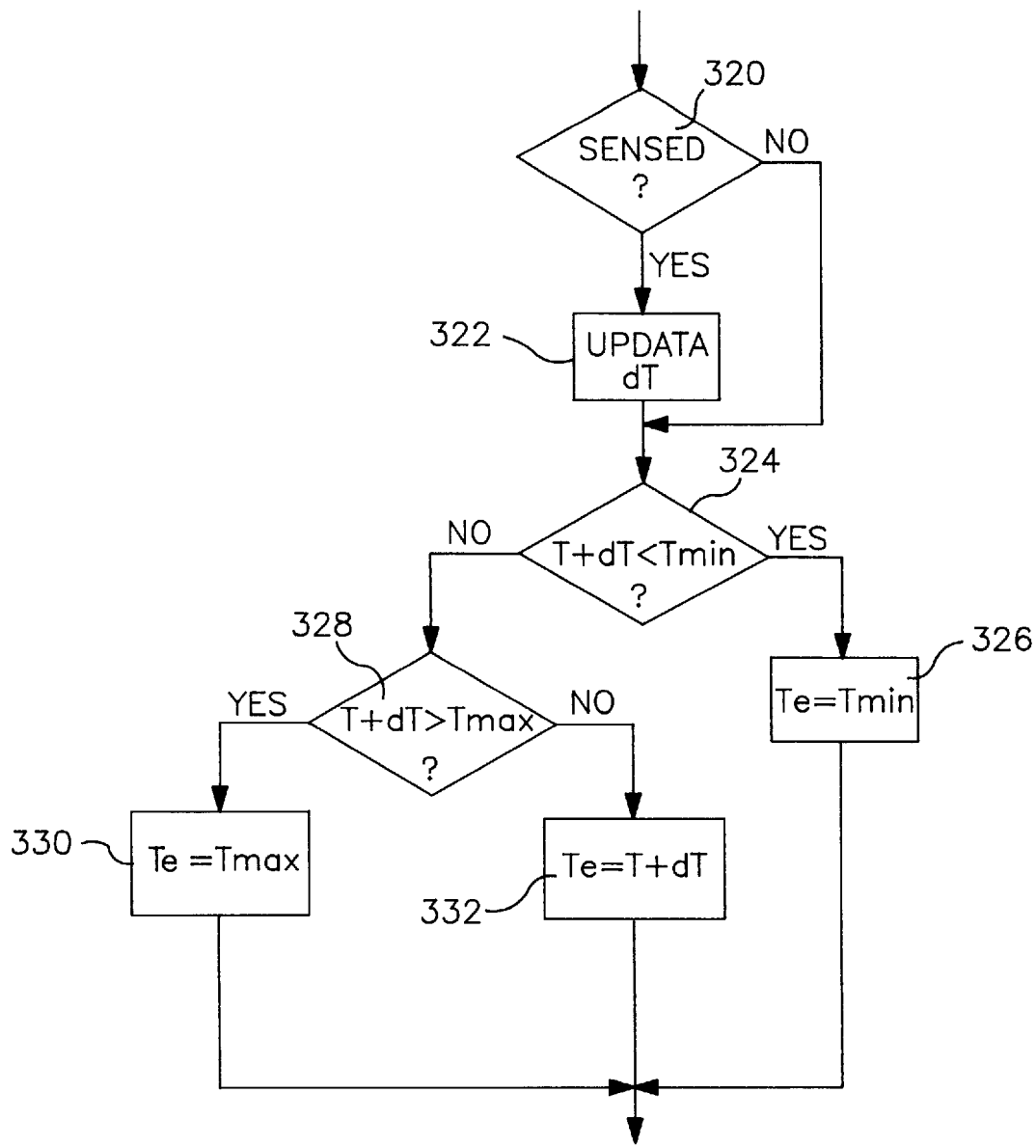
FIG. 7 is a second functional flow chart illustrating a method of controlling the pacing rate in a cardiac pacemaker according to the present invention.

FIG. 7 illustrates the method of calculating the escape interval of a pacemaker according to the present invention. FIG. 7 corresponds to the "SET Te" step in box 56 in FIG. 6. At 320, following the end of the preceding cycle, the microprocessor checks to determine whether the event that ended the cycle was a sensed depolarization. If not, the previously determined value of dT will be retained for use in calculating the duration of the next escape interval. If the event was a sensed depolarization, its value is updated at 322. At 324, the microprocessor checks to see whether T+dT is less than Tmin. If so, Te is set equal to Tmin at 332. If not, the microprocessor checks at 328 to determine whether T+dT is greater than Tmax. If so, Te is set equal to Tmax at 330. If not, Te is set equal to T+dT at 332.

If the alternative implementation discussed above in which the value of dT is updated following each paced or sensed beat is desired, the flow chart of FIG. 7 may be modified by simply deleting the function of checking to determine whether the event that ended the cycle was a sensed event at 320. With this change, the value of dT will be updated following each sensed beat and each paced beat.

In the embodiment described above, sensing is disabled during the refractory period. If, as in some pacemakers, sensing is enabled during the refractory period, the pacemaker is preferably configured so that, as in the disclosed embodiment, updating of the values of dT and of the escape interval occurs only in response to sensed events which re-start the escape interval.

Although the pacemaker described in the specification is a ventricular or atrial inhibited pacemaker, it is believed that the pacing modality discussed herein would also be useful and valuable in the context of a dual chamber pacemaker. For example, the present invention could be embodied in dual chamber pacemakers operating in s VDD, DVI, DDI or DDD modes. As noted above, the present invention may also be embodied in rate responsive pacemakers of the type disclosed in U.S. Pat. No. 4,467,807 issued to Bornzin on Aug. 28, 1984, for a "Rate Adaptive Demand Pacemaker", incorporated herein by reference in its entirety. Such pacemakers vary their escape rate in response to sensing a physiologic parameter indicative of cardiac demand. In this case, it is suggested that the physiologic parameter be used to modulate Tmax and Tmin, decreasing the duration of each with increased sensed demand for cardiac output, with the remainder of the operation of the pacemaker as disclosed above.

In conjunction with the above specification, I claim:

1. A cardiac pacemaker, comprising:

sensing means for sensing depolarizations of a heart, pulse generating means for delivering pacing pulses to the heart; and timing means responsive to said sensing means and coupled to said pulse generating means, said timing means defining escape intervals following sensed depolarizations and delivered pacing pulses and triggering said pulse generating means after expirations of the escape intervals;

cardiac cycle measuring means for measuring and storing durations of cardiac cycles; and control means responsive to said sensing means for adjusting the escape interval determined by said timing means after a sensed depolarization, said control means adjusting the escape interval defined by said timing means to be equal to the duration of a first cardiac cycle measured by said cardiac cycle measuring means, immediately preceding said sensed depolarization, plus an increment of time determined by said control means based on the duration of a second cardiac cycle measured by said cardiac cycle measuring means, preceding the first cardiac cycle.

2. A pacemaker according to claim 1 above wherein said control means comprises means for determining the duration of the increment based on lengths of a series of cycles measured by the cardiac cycle measuring means, preceding the first cardiac cycle.

3. A pacemaker according to claim 2 above wherein said control means comprises means for determining the duration of the increment based on the average duration of the series of cycles measured by the cardiac cycle measuring means, preceding the first cardiac cycle.

4. A pacemaker according to claim 2 above wherein the control means comprises means for increasing the duration of the increment responsive to increases in the durations of the series of cycles measured by said cardiac cycle measuring means, preceding the first cardiac cycle.

5. A pacemaker according to claim 1 or claim 2 or claim 3 or claim 4, wherein the control means comprises means for determining relative prematurity of a sensed depolarization and means for determining the duration of the increment based upon the relative prematurity of the sensed depolarization.

6. A pacemaker according to claim 5, wherein the means for determining prematurity comprises means for comparing durations of the first and second cardiac cycles.

7. A pacemaker according to claim 5, wherein the control means comprises means for decreasing the duration of the increment in response to increases in the relative prematurity of the sensed depolarization.

8. A pacemaker according to claim 5, wherein said control means comprises means responsive to said pulse generating means for adjusting the escape interval determined by said timing means after a delivered pacing pulse, said control means adjusting the escape interval defined by said timing means to be equal to the duration of a cardiac cycle measured by said cardiac cycle measuring means, immediately preceding said pacing pulse, plus the increment determined by said control means following a preceding sensed depolarization.

9. A pacemaker according to claim 5, wherein said control means comprises means responsive to said pulse generating means for adjusting the escape interval determined by said timing means after a delivered pacing pulse, said control means adjusting the escape interval defined by said timing means to be equal to the length of a first cardiac cycle measured by said cardiac cycle measuring means, immediately preceding said pacing pulse plus an increment of time determined by said control means based on the length of a second cardiac cycle preceding the first cardiac cycle.

10. A method of controlling escape interval of a cardiac pacemaker, comprising:

sensing depolarizations of a heart, delivering stimulation pulses to the heart;

defining escape intervals following sensed depolarizations and delivered pacing pulses and triggering said pulse generating means after expirations of the escape intervals;

measuring and storing durations of cardiac cycles; and adjusting the escape interval after a sensed depolarization to be equal to the measured duration of a first cardiac cycle immediately preceding said sensed depolarization, plus an increment of time based on the measured duration of a second cardiac cycle preceding the first cardiac cycle.

11. A method according to claim 10 above wherein said adjusting step comprises determining the duration of the increment based on measured durations of a series of cycles preceding the first cardiac cycle.

12. A method according to claim 11 above wherein said adjusting step comprises determining the duration of the increment based on the average measured durations of the series of cycles preceding the first cardiac cycle.

13. A method according to claim 11 above wherein the adjusting step comprises increasing the duration of the increment responsive to increases in the measured durations of the series of cycles preceding the first cardiac cycle.

14. A method according to claim 10 or claim 11 or claim 12 or claim 13, wherein the adjusting step comprises determining relative prematurity of a sensed depolarization and determining the duration of the increment based upon the relative prematurity of the sensed depolarization.

15. A method according to claim 14, wherein the step of determining prematurity comprises comparing durations of the first and second cardiac cycles.

16. A method according to claim 14, wherein the adjusting step comprises decreasing the duration of the increment in response to increases in the relative prematurity of the sensed depolarization.

17. A method according to claim 14, wherein said adjusting step comprises adjusting the escape interval after a delivered pacing pulse to be equal to the duration of a measured cardiac cycle immediately preceding said pacing pulse, plus the increment determined following a preceding sensed depolarization.

18. A method according to claim 14, wherein said adjusting step comprises adjusting the escape interval after a delivered pacing pulse to be equal to the measured duration of a first cardiac cycle immediately preceding said pacing pulse plus an increment of time based on the length of a second cardiac cycle preceding the first cardiac cycle.

* * * * *